(12) United States Patent
Bluchel et al.

(10) Patent No.: US 9,242,036 B2
(45) Date of Patent: Jan. 26, 2016

(54) SORBENT FOR A DIALYSIS DEVICE

(75) Inventors: Christian Gert Bluchel, Singapore (SG); Yanmei Wang, Singapore (SG); Kim Cheng Tan, Singapore (SG)

(73) Assignee: TEMASEK POLYTECHNIC, Singapore (SG)

( * ) Notice: Subject to any disclaimer, the term of this patent is extended or adjusted under 35 U.S.C. 154(b) by 752 days.

(21) Appl. No.: 13/000,811

(22) PCT Filed: Jun. 22, 2009

(86) PCT No.: PCT/SG2009/000229
§ 371 (c)(1),
(2), (4) Date: Apr. 4, 2011

(87) PCT Pub. No.: WO2009/157877
PCT Pub. Date: Dec. 30, 2009

(65) Prior Publication Data
US 2011/0171713 A1    Jul. 14, 2011

Related U.S. Application Data

(60) Provisional application No. 61/074,997, filed on Jun. 23, 2008.

(51) Int. Cl.
| | |
|---|---|
| *A61M 1/30* | (2006.01) |
| *A61M 1/16* | (2006.01) |
| *B01J 20/06* | (2006.01) |
| *B01J 20/20* | (2006.01) |
| *B01J 20/22* | (2006.01) |
| *B01J 20/28* | (2006.01) |
| *B01J 39/12* | (2006.01) |
| *B01J 41/10* | (2006.01) |
| *A61M 1/28* | (2006.01) |

(52) U.S. Cl.
CPC ............. *A61M 1/1696* (2013.01); *B01J 20/06* (2013.01); *B01J 20/20* (2013.01); *B01J 20/22* (2013.01); *B01J 20/28052* (2013.01); *B01J 39/12* (2013.01); *B01J 41/10* (2013.01); *A61M 1/28* (2013.01)

(58) Field of Classification Search
CPC ........ C12N 11/00; C12N 11/14; C12N 11/02; C12N 11/08; C02F 2003/002; A61K 9/00; A61K 31/00; C12M 1/00; C12M 1/40
See application file for complete search history.

(56) References Cited

U.S. PATENT DOCUMENTS

| | | | |
|---|---|---|---|
| 4,581,141 A | 4/1986 | Ash | |
| 6,579,460 B1 * | 6/2003 | Willis et al. | 210/638 |
| 6,627,164 B1 | 9/2003 | Wong | |
| 6,818,196 B2 | 11/2004 | Wong | |
| 7,033,498 B2 | 4/2006 | Wong | |
| 7,101,519 B2 | 9/2006 | Wong | |
| 7,169,303 B2 * | 1/2007 | Sullivan et al. | 210/321.63 |
| 7,906,093 B2 * | 3/2011 | Wong | 423/308 |
| 8,491,517 B2 | 7/2013 | Karoor et al. | |
| 2007/0179431 A1 | 8/2007 | Roberts et al. | |
| 2007/0213665 A1 * | 9/2007 | Curtin et al. | 604/131 |
| 2008/0051696 A1 | 2/2008 | Curtin et al. | |
| 2012/0037558 A1 | 2/2012 | Karoor et al. | |
| 2014/0001112 A1 | 1/2014 | Karoor et al. | |

FOREIGN PATENT DOCUMENTS

| | | |
|---|---|---|
| EP | 0 003 914 A2 | 9/1979 |
| JP | 2004-525747 A | 8/2004 |
| JP | 2005-508711 A | 4/2005 |
| WO | 02/43859 A2 | 6/2002 |
| WO | 03/041764 A1 | 5/2003 |
| WO | 2007/089855 A2 | 8/2007 |
| WO | 2007/103411 A2 | 9/2007 |

OTHER PUBLICATIONS

International Search Report: PCT/SG2009/000229.
Australian Patent Examination Report No. 1; Appln. No. 2009263045 issued Jul. 18, 2013.
New Zealand Examination Report dated Jan. 19, 2012; Patent Appln. No. 590467.

* cited by examiner

*Primary Examiner* — Robert Yamasaki
*Assistant Examiner* — Teresa E Knight
(74) *Attorney, Agent, or Firm* — Ladas & Parry LLP

(57) ABSTRACT

There is provided a sorbent for removing metabolic waste products from a dialysis liquid, the sorbent comprising a layer of immobilized uremic toxin-treating enzyme particles intermixed with cation exchange particles.

11 Claims, 6 Drawing Sheets

SORBENT FOR A DIALYSIS DEVICE

TECHNICAL FIELD

The present invention relates to a sorbent for use in a dialysis device.

BACKGROUND

Kidneys are vital organs of the humans homeostasis system. Kidneys act as a natural filter in the body which remove toxic metabolic wastes such as urea from the blood. Kidney failure or malfunction may lead to an accumulation of toxins and to an imbalanced electrolyte level in the blood, which may result in undesirable repercussions that are hazardous to an individual's health. In this regard, patients with impaired kidney functionality will usually have to undergo dialysis for the removal of toxic wastes in the blood and for the restoration of the optimal level of electrolytes in the blood.

For the past few years, the predominant form of dialysis used for patients with end-stage renal disease (ESRD) is hemodialysis. Hemodialysis involves the use of an extracorporeal system for the removal of toxins directly from the patient's blood by passing a large amount of the patient's blood through a filtering unit or dialyzer. In conventional hemodialysis processes, patients must spend hours immobilized throughout the duration of the dialysis, encumbering the patient's mobility. Another drawback of hemodialysis is the need to utilize an anticoagulant during the treatment process, which may inevitably increase the risk of internal hemorrhages.

The other form of dialysis used for patient with kidney failure is peritoneal dialysis, most commonly applied in the following two techniques: "continuous ambulatory peritoneal dialysis" (CAPD) and "automated peritoneal dialysis" (APD). In CAPD, fresh dialysate is infused into the patient's abdominal (peritoneal) cavity where, by means of diffusion, metabolic waste and electrolytes in the blood are exchanged with the dialysate across the peritoneal membrane. To allow sufficient diffusion of the electrolytes and metabolic waste to occur, the dialysate is retained in the abdominal (peritoneal) cavity for a couple of hours before removal and replacement (of the spent dialysate) with fresh dialysate. Major drawbacks of continuous ambulatory peritoneal dialysis are a low level of toxin clearance, and the need to continuously replace the spent dialysate, which can be arduous for the patient and disruptive to his/her daily activities.

To overcome the above-mentioned problems of conventional hemodialysis and continuous ambulatory peritoneal dialysis treatments, automated peritoneal dialysis (APD) devices have been developed in recent years. In APD, dialysis is performed at night, or while the patient is resting. The dialysate is exchanged and replaced automatically. This allows for more frequent changes of dialysate and better toxin clearance with minimal interruption to the patient's daily activities.

However, all dialysis techniques described above still suffer from several drawbacks. For example, hemodialysis fails to remove protein-bound toxins, while peritoneal dialysis entails a significant loss of beneficial proteins for the patient. Hemodialysis, CAPD and APD fail to provide optimal clearance for uremic toxins, because of limitation in the volume of dialysate used (due to cost constraints). In cases where the hemodialysis device comprises a regenerating unit, such as a sorbent cartridge that regenerates spent dialysate, the overall size and weight of these dialysis devices are often too large to be portable and therefore do not improve a patients' mobility. Such devices are also cumbersome due to the bulky nature of the sorbent used to ensure adequate removal of the toxins, which is a requirement resulting from the intermittent use of the device. In addition, the flow system of known regenerating hemo-dialysis devices requires a plurality of pumps, which in turn undesirably increases the overall size, weight and power consumption of the device. In alternative forms of these devices proposed for use in peritoneal dialysis, the portability of the automated peritoneal dialysis devices is attempted to be improved by reducing the size of the regenerating units. However, the trade-off for the reduction in size of the regenerating unit is the significant lowering of the efficacy of toxin removal by the regenerating unit or sorbent, which eventually compromises the patients' well being.

There is a need to provide a dialysis device that overcomes or at least ameliorates one or more of the disadvantages described above. Such a device should be portable, relatively light and have high efficacy in removing toxins. Accordingly, there is also a need to provide a regenerating component or sorbent that is compact and has a superior capability of removing toxins and, which can be incorporated into the dialysis device.

SUMMARY OF INVENTION

According to a first aspect, there is provided a sorbent for removing metabolic waste products from a dialysis liquid, the sorbent comprising a layer of immobilized uremic toxin-treating enzyme particles intermixed with cation exchange particles. In one embodiment, the cation exchange particles are ammonia absorbers. The cation exchange particles may also comprise ions of a metal whose phosphate is poorly soluble in water. In one embodiment, there is provided a sorbent for removing metabolic waste products from a dialysis liquid, the sorbent comprising a layer of covalently immobilized uremic toxin-treating enzyme particles intermixed with a water insoluble ammonia absorbent, such as cation exchange particles. Advantageously, the presence in a single composite layer of the cation exchange particles together with the immobilized uremic toxin-treating enzyme particles enhances the workability of the uremic toxin-treating enzyme particles and prevents clogging of the cartridge by unwanted precipitation within the dialysate. The cation exchange particles not only remove unwanted cations, but also serve as a buffer to establish a relatively constant pH range for the enzymatic reaction of the uremic toxin-treating enzyme. Furthermore, the spatial proximity of uremic toxin-treating enzyme and cation exchanger particles may increase the efficacy of the absorption of enzyme produced unwanted cations. A further advantage lies in the covalent immobilization of the uremic toxin-treating enzyme, thereby preventing leakage of the enzyme into the dialysate. Advantageously, this removes the requirement for an additional layer of sorbent for enzyme re-absorption—a drawback of known dialysate regenerating devices, which significantly contributes to the bulkiness of these systems and impairs their biocompatibility.

In one embodiment, the sorbent of the first aspect may be preceded by a layer of organic compound absorber particles, or an organic compound absorber pad. Advantageously, this layer removes enzyme inhibiting substances, thus maintaining the activity and stability of the uremic toxin-treating enzyme. In another embodiment, the sorbent of the first aspect further comprises a layer of cation exchange particles. In one embodiment, the cation exchange particles are ammonia absorbers. The cation exchange particles may also comprise ions of a metal whose phosphate is poorly soluble in water. Advantageously, this layer ensures that any unwanted cations that have escaped from the layer of intermixture of cation exchange particles and immobilized uremic toxin-treating enzyme particles, are removed. In another embodiment, the disclosed sorbent may further comprise a layer of anion exchange particles intermixed with organic compound absorbent particles. The presence of the two layers of intermixtures reduces the overall size and height of the sorbent, facilitates the sorbent production and reduces the overall pressure drop caused by the sorbent when used in the dialysis device. Advantageously, this increases the portability and user comfort of the sorbent without adversely affecting the efficiency with which metabolic waste products are removed by the sorbent.

According to a second aspect, there is provided a sorbent for removing metabolic waste products from a dialysis liquid, the sorbent comprising a layer of cation exchange particles, having an average particle size in the range of 10 microns to 1000 microns. In one embodiment, the cation exchange particles are ammonia absorbers. The cation exchange particles may also comprise ions of a metal whose phosphate is poorly soluble in water. In one embodiment, there is provided a sorbent for removing metabolic waste products from a dialysis liquid, the sorbent comprising covalently immobilized uremic toxin-treating enzyme particles, the particles having an average particle size in the range of 10 to 1000 microns. The sorbent may further comprise ammonia absorbing particles such as cation exchange particles comprising of an amorphous, water-insoluble metal phosphate in protonated and/or sodium counter-ion form, the cation exchange particles having an average particle size in the range of 10 microns to 1000 microns. The sorbent may further comprise anion exchange particles comprising of an amorphous and partly hydrated, water-insoluble metal oxide in its hydroxide, carbonate, acetate, and/or lactate counter-ion form, the anion exchange particles having an average particle size of 10 microns to 1000 microns. The sorbent may further comprise organic compound absorber particles having an average particle size of 10 to 1000 microns. It has been found by the inventors that the use of this specific particle size range of the uremic toxin-treating enzyme particles, cation exchange particles, anion exchange particles and organic compound absorber particles greatly improves the efficacy of metabolic waste products removal, while allowing for a favorably low flow resistance and minimal solubility of the respective sorbent materials. Advantageously, the dialysate that has passed through the sorbent may be essentially free of any unwanted ions and metabolic waste products.

According to a third aspect, there is provided a sorbent for removing metabolic waste products from a dialysis liquid, the sorbent comprising:

a primary layer of immobilized uremic toxin-treating enzyme particles;

a secondary layer of cation exchange particles having an average particle size in the range of 10 microns to 1000 microns; and a tertiary layer and quaternary layer, at least one of said layers comprising anion exchange particles while the other layer comprising organic compound absorber particles. In one embodiment, the cation exchange particles are ammonia absorbers. The cation exchange particles may also comprise ions of a metal whose phosphate is poorly soluble in water.

In one embodiment, there is provided a sorbent for removing metabolic waste products from a dialysis liquid, the sorbent comprising:

a primary layer of organic compound absorbing particles or an organic compound absorbing pad;

a secondary layer of immobilized uremic toxin-treating enzyme particles;

a tertiary layer of cation exchange particles comprising of an amorphous, water-insoluble metal phosphate in protonated- and/or sodium counter-ion form, the cation exchange particles having an average particle size in the range of 10 microns to 1000 microns; and a quaternary layer and quinary layer, at least one of said layers comprising anion exchange particles comprising of an amorphous and partly hydrated, water-insoluble metal oxide in its hydroxide-, carbonate-, acetate-, and/or lactate-counter-ion form, the anion exchange particles having an average particle size of 10 microns to 1000 microns while the other layer comprising organic compound absorber particles having an average particle size of 10 to 1000 microns.

In another embodiment, there is provided a sorbent for removing metabolic waste products from a dialysis liquid, the sorbent comprising:

a primary layer of immobilized uremic toxin-treating enzyme particles;

a secondary layer of cation exchange particles comprising ions of a metal whose phosphate is poorly soluble in water, the cation exchange particles having an average particle size in the range of 10 microns to 1000 microns;

a tertiary layer of anion exchange particles; and a quaternary layer of organic compounds absorber particles.

In another embodiment, there is provided a sorbent for removing metabolic waste products from a dialysis liquid, the sorbent comprising:

a primary layer of organic compound absorbent particles or an organic compound absorbent pad a secondary layer of immobilized uremic toxin-treating enzyme particles;

a tertiary layer of cation exchange particles comprising of an amorphous, water-insoluble metal phosphate in protonated- and/or sodium counter-ion form, the cation exchange particles having an average particle size in the range of 10 microns to 1000 microns;

a quaternary layer of anion exchange particles; and a quinary layer of organic compounds absorber particles.

In another embodiment, there is provided a sorbent for removing metabolic waste products from a dialysis liquid, the sorbent comprising:

a primary layer of organic compound absorbing particles or an organic compound absorbing pad;

a secondary layer of immobilized uremic toxin-treating enzyme particles intermixed with cation exchange particles;

a tertiary layer of cation exchange particles intermixed with anion exchange particles; and a quaternary layer of organic compound absorber particles.

In another embodiment, there is provided a sorbent for removing metabolic waste products from a dialysis liquid, the sorbent comprising:

a primary layer of organic compound absorbing particles or an organic compound absorbing pad;

a secondary layer of immobilized uremic toxin-treating enzyme particles intermixed with cation exchange particles and anion exchange particles;

a tertiary layer of organic compound absorber particles.

In another embodiment, there is provided a sorbent for removing metabolic waste products from a dialysis liquid, the sorbent comprising:

a primary layer of organic compound absorbing particles;

a secondary layer of immobilized uremic toxin-treating enzyme particles intermixed with cation exchange particles and anion exchange particles.

In another embodiment, there is provided a sorbent for removing metabolic waste products from a dialysis liquid, the sorbent comprising:

immobilized uremic toxin-treating enzyme particles intermixed with cation exchange particles, anion exchange particles, and organic compound absorbing particles.

DEFINITIONS

The following words and terms used herein shall have the meaning indicated:

The term "sorbent" as used herein broadly refers to a class of materials characterized by their ability to absorb the desired matter of interest.

The term "non-toxic" as used herein refers to a substance that causes little to no adverse reactions when present in the human body.

The term "contaminants" in the context of this specification, means any constituents, typically toxic constituents, within a dialysate that are generally harmful to human health and which are desirable to be removed in a dialysate detoxification process. Typical contaminants include, but are not limited to ammonium, phosphates, urea, creatinine and uric acid.

The term "cation exchange particles" as used herein refers to particles capable of capturing or immobilizing cationic or positively charged species when contacted with such species, typically by passing a solution of the positively charged species over the surface of the particles.

The term "anion exchange particles" as used herein refers to particles capable of capturing or immobilizing anionic or negatively charged species when contacted with such species, typically by passing a solution of the negatively charged species over the surface of the particles.

The term "biocompatible" as used herein refers to the property of a material that does not cause adverse biological reactions to the human or animal body.

The term "particle size" refers to the diameter or equivalent diameter of the particle. The term "average particle size" means that a major amount of the particles will be close to the specified particle size although there will be some particles above and some particles below the specified size. The peak in the distribution of particles will have a specified size. Thus, for example, if the average particle size is 50 microns, there will exist some particles which are larger and some particles which are smaller than 50 microns, but the major amount of the particles, preferably 80%, more preferably 90%, will be at approximately 50 microns in size and a peak in the distribution of particles will be 50 microns.

The term "regenerate" as used herein refers to the action of detoxifying dialysate by absorption of uremic toxins.

The term "reconstitute" as used herein refers to the action of converting regenerated dialysate to essentially the same state and chemical composition as fresh peritoneal dialysate prior to dialysis.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DETAILED DISCLOSURE OF EMBODIMENTS

Exemplary, non-limiting embodiments of a sorbent for a dialysis device will now be disclosed. The sorbent may be capable of removing metabolic waste, such as urea, from the fluid in contact with said sorbent.

In one embodiment, the sorbent comprises a primary layer of immobilized uremic toxin-treating enzyme particles intermixed with cation exchange particles; a secondary layer of cation exchange particles; and a tertiary layer of anion exchange particles intermixed with organic compounds absorber particles. In one embodiment, the cation exchange particles are ammonia absorbers. The cation exchange particles may also comprise ions of a metal whose phosphate is poorly soluble in water. In one embodiment, the sorbent comprises the secondary layer bound between the primary and tertiary layers, wherein in use, dialysis fluid passes from said primary layer to said tertiary layer via said secondary layer. An additional layer of organic compound absorber may also be included in the sorbent.

In another embodiment, the sorbent comprises a primary layer of immobilized uremic toxin-treating enzyme particles; a secondary layer of cation exchange particles, said cation exchange particles comprising ions of a metal whose phosphate is poorly soluble in water; a tertiary layer and quaternary layer, wherein said tertiary layer and quaternary layers are respectively a layer of anion exchange particles and a layer of organic compound absorber particles, or vice versa. An additional layer of organic compound absorber may also be included in the sorbent.

In one embodiment, the sorbent comprises the primary layer bound to the secondary layer, the secondary layer bound to the tertiary layer and the tertiary layer bound to the quaternary layer, wherein in use, dialysis fluid passes from said primary layer to said secondary layer, from said secondary layer to said tertiary layer, and from said tertiary layer to said quaternary layer. In one embodiment, the secondary layer is disposed between said primary and said tertiary layer and said tertiary layer is disposed between said secondary layer and said quaternary layer.

In one embodiment, the sorbent comprises a primary layer of organic compound absorber particles or pad, followed by a secondary layer of immobilized uremic toxin-treating enzyme particles intermixed with ammonia absorbing particles such as cation exchange particles comprising of an amorphous, water-insoluble metal phosphate in protonated- and/or sodium counter-ion form; a tertiary layer of ammonia absorbing particles, such as cation exchange particles comprising of an amorphous, water-insoluble metal phosphate in protonated- and/or sodium counter-ion form; and a quaternary layer of anion exchange particles comprising of an amorphous and partly hydrated, water-insoluble metal oxide in its hydroxide-, carbonate-, acetate-, and/or lactate-counter-ion form, intermixed with organic compounds absorber particles.

In one embodiment, the sorbent comprises the secondary layer bound between the primary and tertiary layers and the tertiary layer bound between the secondary and quaternary layers, wherein in use, dialysis fluid passes from said primary layer to said quaternary layer via said secondary and tertiary layers.

In another embodiment, the sorbent comprises a primary layer of organic molecule absorber particles or pad, a secondary layer of immobilized uremic toxin-treating enzyme particles; a tertiary layer of cation exchange particles comprising of an amorphous, water-insoluble metal phosphate in protonated- and/or sodium counter-ion form; a quaternary layer and quinary layer, wherein said quaternary layer and quinary layers are respectively a layer of anion exchange particles comprising of an amorphous and partly hydrated, water-insoluble metal oxide in its hydroxide-, carbonate-, acetate-, and/or lactate-counter-ion form, and a layer of organic compound absorber particles, or vice versa.

In one embodiment, the sorbent comprises the primary layer bound to the secondary layer, the secondary layer bound to the tertiary layer, the tertiary layer bound to the quaternary layer and the quaternary layer bound to the quinary layer, wherein in use, dialysis fluid passes from said primary layer to said secondary layer, from said secondary layer to said tertiary layer, from said tertiary layer to said quaternary layer, and from said quaternary layer to said quinary layer. In one embodiment, the secondary layer is disposed between said primary and said tertiary layer, said tertiary layer is disposed between said secondary layer and said quaternary layer, and said quaternary layer is disposed between said tertiary and said quinary layer.

The uremic toxin-treating enzyme particles may be capable of converting urea to ammonium carbonate. In one embodiment the uremic toxin-treating enzyme is at least one of urease, uricase and creatininase. In a preferred embodiment, the uremic toxin-treating enzyme is urease. In one embodiment, the urease may be replaced by any material that is able to convert urea to products that can be absorbed by a sorbent. Preferably, the material is able to convert urea to ammonium carbonate.

In one embodiment, the ions of a metal whose phosphate is poorly soluble in water are ions of metals selected from the group of titanium, zirconium, hafnium and combinations thereof. In one embodiment, the ions of a metal whose phosphate is poorly soluble in water is zirconium.

In one embodiment, the cation exchanger particles comprises of an amorphous, water-insoluble metal phosphate in protonated- and/or sodium counter-ion form, wherein the metal may be selected from the group consisting of titanium, zirconium, hafnium and combinations thereof. In one embodiment, the metal is zirconium.

Poorly soluble phosphates are to be understood here as phosphates having a solubility not higher than 10 mg/l in water. Preferably, the cation exchange particles are zirconium phosphate particles.

The anion exchange particles may comprise of an amorphous and partly hydrated, water-insoluble metal oxide in its hydroxide-, carbonate-, acetate-, and/or lactate-counter-ion form, wherein the metal may be selected from the group consisting of titanium, zirconium, hafnium and combinations thereof. In one embodiment, the metal is zirconium.

The anion exchange particles may be zirconium oxide particles. Preferably, the anion exchange particles are hydrous zirconium oxide particles.

The organic compounds absorber may be selected from the group consisting, amongst others, of activated carbons, molecular sieves, zeolites and diatomaceous earth. The organic compounds absorber particles may be activated carbon particles. In one embodiment, the organic compound absorber in the primary layer is an activated carbon filter pad. In another embodiment, the organic compound absorber comprises activated carbon particles.

The urease may be immobilized urease. The urease may be immobilized on any known support material, which can provide immobilization for the urease particles. In one embodiment, the support material is a biocompatible substrate. The biocompatible material may be a carbohydrate-based polymer, an organic polymer, a polyamide, a polyester, or an inorganic polymeric material. The biocompatible substrate may be a homogenous substrate made up of one material or a composite substrate made up of at least two materials. The biocompatible substrate may be at least one of cellulose, Eupergit, silicium dioxide (e.g. silica gel), zirconium phosphate, zirconium oxide, nylon, polycaprolactone and chitosan.

In one embodiment, the immobilization of urease on the biocompatible substrate is carried out by immobilization techniques selected from the group consisting of glutaric aldehyde activation, activation with epoxy groups, epichlorohydrin activation, bromoacetic acid activation, cyanogen bromide activation, thiol activation, and N-hydroxysuccinimide and diimide amide coupling. The immobilization techniques used may also involve the use of silane-based linkers such as (3-aminopropyl)triethoxysilane, (3-glycidyloxypropyl)trimethoxysilane or (3-mercaptopropyl)trimethoxysilane. The surface of the biocompatible substrate may be further functionalized with a reactive and/or stabilizing layer such as dextran or polyethyleneglycol, and with suitable linker- and stabilizer molecules such as ethylenediamine, 1,6-diaminohexane, thioglycerol, mercaptoethanol and trehalose. Urease can be used in purified form, or in the form of crude extract of Jack Beans or other suitable urease sources.

In one embodiment, the urease particles have an average particle size in the range of from about 10 microns to about 1000 microns, about 100 microns to about 900 microns, about 200 microns to about 900 microns, about 300 microns to about 800 microns, about 400 microns to about 700, 500 microns to about 600 microns, about 25 microns to about 250 microns, about 25 microns to about 100 microns, about 250 microns to about 500 microns, about 250 microns to about 1000 microns, about 125 microns to about 200 microns, about 150 microns to about 200 microns, about 100 microns to about 175 microns, and about 100 microns to about 150 microns.

In one embodiment, 1000 to 10000 units of urease are immobilized on said biocompatible substrate. The overall weight of immobilized urease and the substrate ranges from about 0.5 g to about 30 g.

In one embodiment, the urease may be replaced by any material that is able to convert urea to a non-toxic compound. Preferably, the material is able to convert urea to ammonium carbonate.

The zirconium phosphate particles may have an average particle size in the range of from about 10 microns to about 1000 microns, about 100 microns to about 900 microns, about 200 microns to about 900 microns, about 300 microns to about 800 microns, about 400 microns to about 700, 500 microns to about 600 microns, about 25 microns to about 200 microns or from about 25 microns to about 150 microns or from about 25 microns to about 80 microns or from about 25 microns to about 50 microns or from about 50 microns to about 100 microns or from about 125 microns to about 200 microns, or from about 150 microns to about 200 microns, or from about 100 microns to about 175 microns, or from about 100 microns to about 150 microns or from about 150 microns to about 500 microns, or from about 250 microns to about 1000 microns.

The zirconium phosphate particles may be immobilized on any known support material, which can provide immobilization for the zirconium phosphate particles. In one embodiment, the support material is a biocompatible substrate. In one embodiment, the immobilization of the zirconium phosphate particles is a physical compaction of the particles into a predetermined volume. In one embodiment, the immobilization of the zirconium phosphate particles is achieved by sintering zirconium phosphate, or a mixture of zirconium phosphate and a suitable ceramic material. The biocompatible substrate may be a homogenous substrate made up of one material or a composite substrate made up of at least two materials. The biocompatible material may be a carbohydrate-based polymer, an organic polymer, a polyamide, a polyester, a polyacrylate, a polyether, a polyolefin or an inorganic polymeric or ceramic material. The biocompatible substrate may be at least one of cellulose, Eupergit, silicium dioxide, nylon, polycaprolactone and chitosan.

In one embodiment, the zirconium phosphate particles may be replaced by any particles that are able to absorb ammonium ions and other cations. Preferably, the particles are able to absorb cations selected from the group comprising ions of ammonium, calcium, magnesium, sodium and potassium. The ammonia absorbant particles may also release ions such as sodium and hydrogen in exchange for absorbed ammonium ions and other cations. In one embodiment, the ammonia absorbant also functions as a buffer for establishing a constant pH for urease reaction.

The zirconium oxide particles may have an average particle size in the range of from about 10 microns to about 1000 microns, about 100 microns to about 900 microns, about 200 microns to about 900 microns, about 300 microns to about 800 microns, about 400 microns to about 700, 500 microns to about 600 microns, about 10 microns to about 200 microns or from about 10 microns to about 100 microns or from about 10 microns to about 30 microns or from about 10 microns to about 20 microns or from about 20 microns to about 50 microns or from about 25 microns to about 50 microns or from about 30 microns to about 50 microns or from about 40 microns to about 150 microns or from about 80 microns to about 120 microns or from about 160 microns to about 180 or from about 25 microns to about 250 or from about 250 microns to about 500 or from about 250 microns to about 1000.

The zirconium oxide particles may be immobilized on any known support material which can provide immobilization for the zirconium oxide particles. In one embodiment, the immobilization of the zirconium phosphate particles is a physical compaction of the particles into a predetermined volume. In one embodiment, the immobilization of the zirconium oxide particles is achieved by sintering zirconium oxide, or a mixture of zirconium oxide and a suitable ceramic material. In one embodiment, the support material is a biocompatible substrate. The biocompatible material may be a carbohydrate-based polymer, an organic polymer, a polyamide, a polyester, a polyacrylate, a polyether, a polyolefin or an inorganic polymeric or ceramic material. The biocompatible substrate may be at least one of cellulose, Eupergit, silicium dioxide, nylon, polycaprolactone and chitosan.

In one embodiment, the zirconium oxide particles may be replaced by any particles that are able to absorb phosphate ions and other anions. Preferably, the particles are able to absorb anions selected from the group comprising ions of phosphate, fluoride, nitrate and sulphate. The zirconium oxide particles may also release ions such as acetate, lactate, bicarbonate and hydroxide in exchange for the anions absorbed. In one embodiment, the zirconium oxide particles are also good binders for iron, aluminum and heavy metals selected from the group consisting of arsenic, bismuth, cadmium, cobalt, copper, lead, mercury, nickel, palladium and silver.

The activated carbon particles may have an average particle size in the range of from about 10 microns to about 1000 microns, about 10 microns to about 250 microns, about 20 microns to about 200 microns, about 25 microns to about 150 microns, about 50 microns to about 100 microns, about 25 microns to about 250 microns or from about 100 microns to about 200 microns or from about 100 microns to about 150 microns or from about 150 microns to about 300 microns or from about 200 microns to about 300 microns or from about 400 microns to about 900 microns or from about 500 microns to about 800 microns or from about 600 microns to about 700 microns or from about 250 microns to about 500 microns or from about 250 microns to about 1000 microns.

In one embodiment, the activated carbon particles may be replaced by any particles that are able to absorb organic compounds. Preferably, the particles are able to absorb organic compounds and/or organic metabolites selected from the group comprising creatinine, uric acid and other small and medium sized organic molecules without releasing anything in exchange. The activated carbon particles may also be physically compacted into a predetermined volume for the purpose of space economy. In one embodiment, the activated carbon particles are physically compacted into an activated carbon filter pad.

In one embodiment, the sorbent is housed in at least one cartridge. The sorbent cartridges may be configured such that they are easily removable from the dialysis device. The sorbent cartridge may also be compact and made of a material that is resistant to wear and tear. The cartridge may be made from resilient, chemically and biologically inert materials. The cartridge may also be able to withstand the pressure within the flow system of the dialysis device without leakage. The cartridge may be made from material which can withstand sterilization conditions such as heat sterilization, ethylene oxide sterilization and sterilization with ionizing radiation. In one embodiment, the sorbent cartridges are made of polycarbonate. The sorbent cartridges may also be made of polypropylene or polyethylene. In one embodiment, filter pads and filter papers may also be located at the in- and outlet of the sorbent cartridges and/or between the individual layers within the sorbent, to filter off any particles arising from the layers of the sorbent.

BRIEF DESCRIPTION OF DRAWINGS

The accompanying drawings illustrate disclosed embodiments and serve to explain the principles of the disclosed embodiments. It is to be understood, however, that the drawings are designed for purposes of illustration only, and not as a definition of the limits of the invention.

FIG. 2a is an isometric view of a CAD of the sorbent cartridge and FIG. 2b is a cross sectional view of the sorbent cartridge of FIG. 2a.

DETAILED DESCRIPTION

Figure 1A:
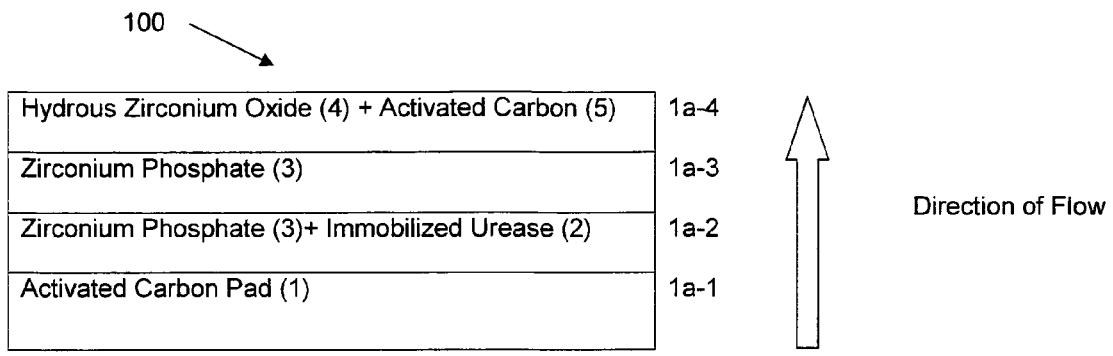
FIG. 1a shows the layout of one embodiment of the sorbent for a dialysis device.

Referring to FIG. 1a, there is shown one embodiment of the sorbent (100) used in the disclosed dialysis device. The first layer (1a-1) of the sorbent (100) comprises an activated carbon pad (1).

The second layer (1a-2) of the sorbent (100) is arranged in series, adjacent to the first layer (1a-1), and comprises of a mixture of immobilized urease (2) and zirconium phosphate particles (3). Purified urease obtained from Jack Bean, crude Jack Bean powder or other sources (such as bacterial, recombinant, thermostable urease mutants, etc.) is covalently immobilized. The solid support material or substrate used is cellulose. The immobilized urease (2) is in the form of particles with particle sizes in the range of 25 microns to 200 microns. The total weight range of the immobilized urease particles used is in the range of from 0.5 grams to 30 grams. The zirconium phosphate particles (3) have sizes from 25 microns to 250 microns, obtained from MEI, New Jersey, United States of America. The total weight range of the zirconium phosphate particles (3) is from about 100 grams to 1000 grams.

The third layer (1a-3) of the sorbent (100) is arranged in series, adjacent to the second layer (1a-2). The third layer (1a-3) comprises zirconium phosphate particles (3) of sizes from 25 microns to 250 microns. The total weight range of the zirconium phosphate particles (3) is from about 100 grams to 1000 grams.

The fourth layer (1a-4) of the sorbent (100) is arranged in series, adjacent to the third layer (1a-3). The fourth layer (1a-4) comprises a mixture of hydrous zirconium oxide particles (4) and activated carbon particles (5). The zirconium oxide particles (4) have sizes from 10 microns to 250 microns, obtained from MEI, New Jersey, United States of America. The total weight range of the zirconium oxide particles (4) is from about 10 grams to 100 grams. The activated carbon particles (5) have sizes from 50 microns to 300 microns, obtained from Calgon Carbon Corporation of Pittsburgh, Pa., United States of America. The total weight range of the activated carbon particles (5) is from about 20 grams to 200 grams.

When in use, the sorbent (100) is arranged in the dialysis device such that the direction of the dialysate flow is from the first layer (1a-1) to the fourth layer (1a-4) as shown by the arrow. As the dialysate passes into the first layer (1a-1), the activated carbon pad (1a-1) removes enzyme inhibiting substances, such as oxidants and/or heavy metals, thus maintaining the activity and stability of the uremic toxin-treating enzyme. Furthermore, this layer also removes toxic organic compounds, such as uremic toxins from the spent dialysate.

As the dialysate passes into the second layer (1a-2), the mixture of immobilized urease (2) and zirconium phosphate particles (3) removes urea and ammonium ions from the dialysate. In addition, as the zirconium phosphate particles (3) not only exchange ions but also act as a buffer, the pH conditions around the urease (2) are kept stable, thereby protecting the urease activity and extending its life time. When the dialysate passes through the second layer (1a-2) and enters the intermediate third layer (1a-3), the zirconium phosphate particles (3) present in this layer, quantitatively remove all ammonium ions formed in the second layer (1a-2). After which, the dialysate passes into the fourth layer (1a-4). The mixture of hydrous zirconium oxide particles (4) and activated carbon particles (5) removes any phosphate ions produced by the patient or leached from the zirconium phosphate particles (3) in the second (1a-2) and/or third (1a-3) layer. The mixture also removes creatinine, uric acid and other uremic toxins present in the dialysate. The combination of the different layers in the sorbent (100) improves the overall efficacy of toxin removal and reduces the overall size of the sorbent (100).

Figure 1B:
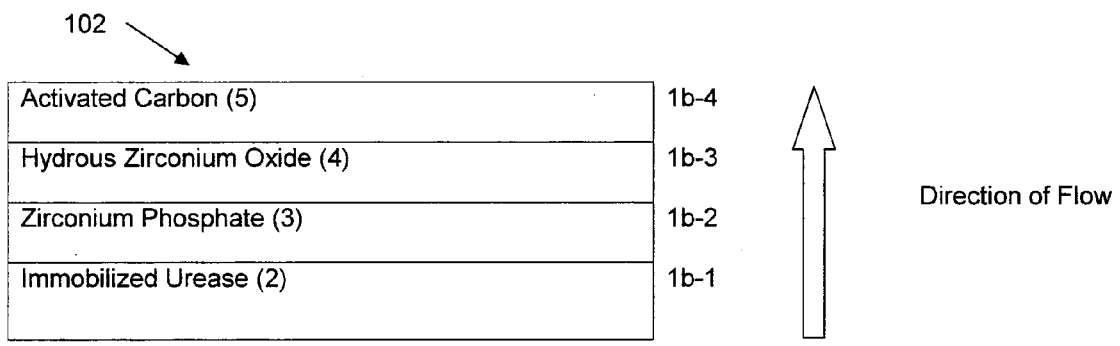
FIG. 1b-1g shows the layout of other different embodiments of the sorbent for a dialysis device.

Referring now to FIG. 1b, there is shown a second embodiment of the sorbent (102) used. The immobilized urease (2), zirconium phosphate particles (3), hydrous zirconium oxide particles (4), activated carbon particles (5) and the respective substrates used for the following layers are the same as those described above for FIG. 1a.

The first layer (1b-1) of the sorbent (102) comprises immobilized urease (2). The urease (2) used is in the form of particles with particle sizes in the range of 25 microns to 200 microns. The total weight of the urease particles used is in the range of from 0.5 grams to 30 grams.

The second layer (1b-2) of the sorbent (102) is arranged in series, adjacent to the first layer (1b-1). The second layer (1b-2) comprises zirconium phosphate particles (3) of sizes from 25 microns to 250 microns. The total weight range of the zirconium phosphate particles (3) is from about 100 grams to 1000 grams.

The third layer (1b-3) of the sorbent (102) is arranged in series, adjacent to the second layer (1b-2). The third layer (1b-3) comprises hydrous zirconium oxide particles (4) of sizes from 10 microns to 250 microns. The total weight range of the zirconium oxide particles (4) is from about 10 grams to 100 grams.

The fourth layer (1b-4) of the sorbent (102) is arranged in series, adjacent to the third layer (1b-3). The fourth layer (1b-4) comprises activated carbon particles (5) of sizes from 25 microns to 300 microns. The total weight range of the activated carbon particles (5) is from about 20 grams to 200 grams.

When in use, the sorbent (102) is arranged in the dialysis device such that the direction of the dialysate flow is from the first layer (1b-1) to the fourth layer (1b-4) as shown by the arrow.

When the dialysate enters the first layer (1b-1), the immobilized urease (2) breaks down urea present in the dialysate to ammonium carbonate, hence releasing ammonium and bicarbonate ions into the dialysate. As the dialysate passes into the second layer (1b-2), the zirconium phosphate particles (3) absorb ammonium cations arising from the decomposition of urea by the first layer (1b-1). The zirconium phosphate particles (3) act as a cation exchanger to absorb other cations such as calcium, potassium and magnesium, releasing sodium and hydrogen in exchange. As the size of the zirconium phosphate particles (3) used is in the range of 25 microns to 250 microns, the absorption of the unwanted cations and the flow resistance of the sorbent is in the optimum range. This ensures that the dialysate exiting from the layer of zirconium phosphate particles (3) is essentially free of any unwanted cations. The dialysate then passes into the third layer (1b-3) and the hydrous zirconium oxide particles (4) remove any phosphate ions produced by the patient or leached from the zirconium phosphate particles (3) in the second layer (1b-2). In summary, the hydrous zirconium oxide particles (4) act as an anion exchanger by binding anions such as phosphate and fluoride and releases acetate and hydroxide ions in exchange. In addition, the hydrous zirconium oxide particles (4) are also good binders for iron, aluminum and heavy metals. After passing the layer of hydrous zirconium oxide particles (4), the dialysate enters the fourth layer (1b-4) and the activated carbon (5) resident in the fourth layer (1b-4) absorbs organic metabolites such as creatinine, uric acid and other small or medium sized organic molecules from the dialysate without releasing anything in exchange.

Figure 1C:
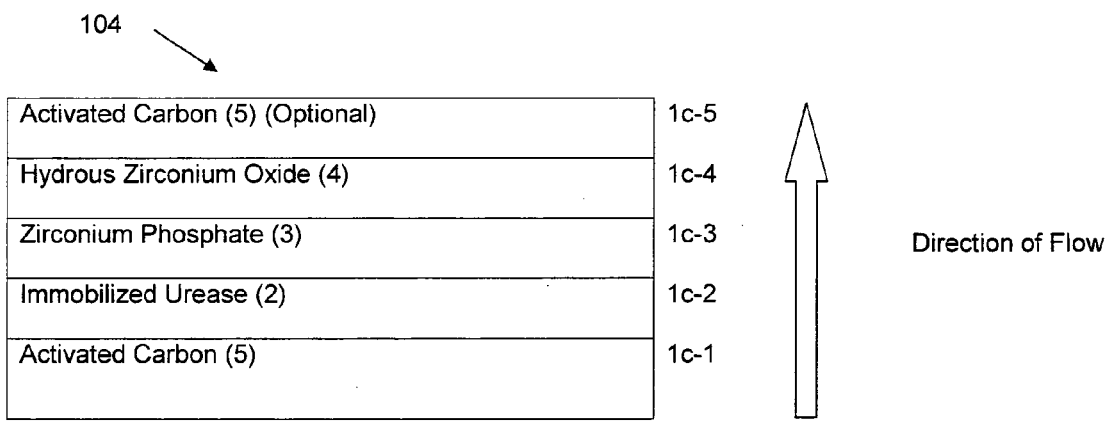

Referring now to FIG. 1c, there is shown another embodiment of the sorbent (104) used. The activated carbon particles (5), immobilized urease particles (2), zirconium phosphate particles (3), hydrous zirconium oxide particles (4) and the respective substrates used for the following layers are the same as those described above for FIG. 1a.

The first layer (1c-1) comprises activated carbon particles (5) of sizes from 25 microns to 300 microns. The total weight range of the activated carbon particles (5) is from about 20 grams to 200 grams.

The second layer (1c-2) of the sorbent (104) contains immobilized urease and is arranged in series, adjacent to the first layer (1c-1). The immobilized urease (2) is in the form of particles with particle sizes in the range of 25 microns to 200 microns. The total weight of the urease particles is in the range of from 0.5 grams to 30 grams.

The third layer (1c-3) of the sorbent (104) is arranged in series, adjacent to the second layer (1c-2). The third layer (1c-3) comprises zirconium phosphate particles (3) of sizes from 25 microns to 250 microns. The total weight range of the zirconium phosphate particles (3) is from about 100 grams to 1000 grams.

The fourth layer (1c-4) of the sorbent (104) is arranged in series, adjacent to the third layer (1c-3). The fourth layer (1c-4) comprises hydrous zirconium oxide particles (4). The zirconium oxide particles (4) have sizes from 10 microns to 250 microns. The total weight range of the zirconium oxide particles (4) is from about 10 grams to 100 grams.

The optional fifth layer (1c-5) of the sorbent (104) is arranged in series, adjacent to the fourth layer (1c-4). When present, the fifth layer (1c-5) comprises activated charcoal (5). The activated carbon particles (5) have sizes from 25 microns to 300 microns. The total weight range of the activated carbon particles (5) is from about 20 grams to 200 grams.

When in use, the sorbent (104) is arranged in the dialysis device such that direction of the dialysate flow is from the first layer (1c-1) to the fourth layer (1c-4) as shown by the arrow. As the dialysate passes into the first layer (1c-1), this layer removes enzyme inhibiting substances and toxic organic compounds, including uremic toxins, same as the activated carbon pad described above (FIG. 1a).

As the dialysate passes into the second layer (1c-2), the immobilized urease (2) degrades urea to ammonium ions and carbonate/bicarbonate ions. When the dialysate passes through the second layer (1c-2) and enters the third layer (1c-3), the zirconium phosphate particles (3) remove ammonium ions from the dialysate. When the dialysate moves forward and enters the fourth layer (1c-4), the hydrous zirconium oxide particles (4) remove any phosphate ions produced by the patient or leached from the zirconium phosphate particles (3) in the third layer (1c-3). As the dialysate moves forward and leaves the fourth layer (1c-4), it may enter a fifth layer (1c-5) of activated carbon particles (5). Where present, this fifth layer (1c-5) removes creatinine, uric acid and other uremic toxins present in the dialysate.

Figure 1D:
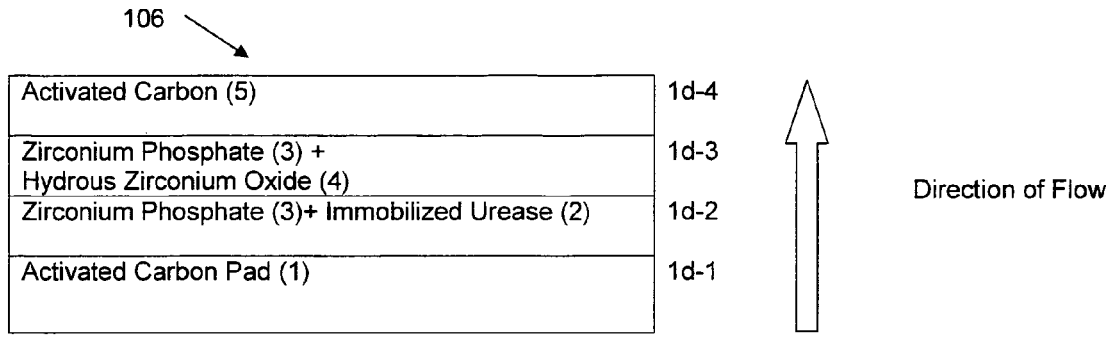

Referring now to FIG. 1d, there is shown another embodiment of the sorbent (106) used. The activated carbon pad (1), immobilized urease (2), zirconium phosphate particles (3), hydrous zirconium oxide particles (4), activated carbon particles (5) and the respective substrates used for the following layers are the same as those described above for FIG. 1a.

Arranged in series, an activated carbon pad (1) in the first layer (1d-1), a mixture of the immobilized urease particles (2) and zirconium phosphate particles (3) in the second layer (1d-2) of the sorbent (106) are the same as those of the first two layers (1b-1 and 1b-2) elaborated in the description for FIG. 1a.

The third layer (1d-3) of the sorbent (106) is arranged in series, adjacent to the second layer (1d-2). The third layer (1d-3) comprises a mixture of zirconium phosphate particles (3) and hydrous zirconium oxide particles (4). The total weight range of the zirconium phosphate particles (3) is from about 100 grams to 1000 grams. The total weight range of the hydrous zirconium oxide particles (4) is from about 10 grams to 100 grams.

The fourth layer (1d-4) of the sorbent (106) is arranged in series, adjacent to the third layer (1d-3). The fourth layer (1d-4) comprises activated carbon particles (5) which is same to that (1b-4) of FIG. 1b. The total weight range of the activated carbon particles (5) is from about 20 grams to 200 grams.

When in use, the sorbent (106) is arranged in the dialysis device such that direction of the dialysate flow is from the first layer (1d-1) to the fourth layer (1d-4) as shown by the arrow. As the dialysate passes through the first layer (1d-1), this layer removes enzyme inhibiting substances and toxic organic compounds, including uremic toxins, same as the description of the activated carbon pad above (FIG. 1a). When the dialysate enters the second layer (1d-2), the mixture of the urease particles (2) and zirconium phosphate particles (3), same to those descriptions in the section of FIG. 1a, remove urea, ammonium ions and other cations, i.e. calcium, magnesium and potassium in the same way. When the dialysate moves into the third layer (1d-3), the mixture of zirconium phosphate particles (3) and hydrous zirconium oxide particles removes said cations escaping from the second layer (1d-2) as well as phosphate and other unwanted anions. The spatial proximity of zirconium phosphate particles (3) and hydrous zirconium oxide particles (4) may facilitate the re-absorption of leaked phosphate. More advantageously, mixing of both types of ion exchangers in one combined layer significantly improves the performance of both particles as a buffer, thus producing more consistent pH conditions in the dialysate throughout the sorbent's use. Meanwhile this mixture also reduces the size of the sorbent (106) without compromising the toxin removal capability. When the dialysate passes into the final layer (1d-4) of the sorbent (106), the activated carbon (5) further absorbs creatinine, uric acid and other uremic toxins present in the spent dialysate.

Figure 1E:
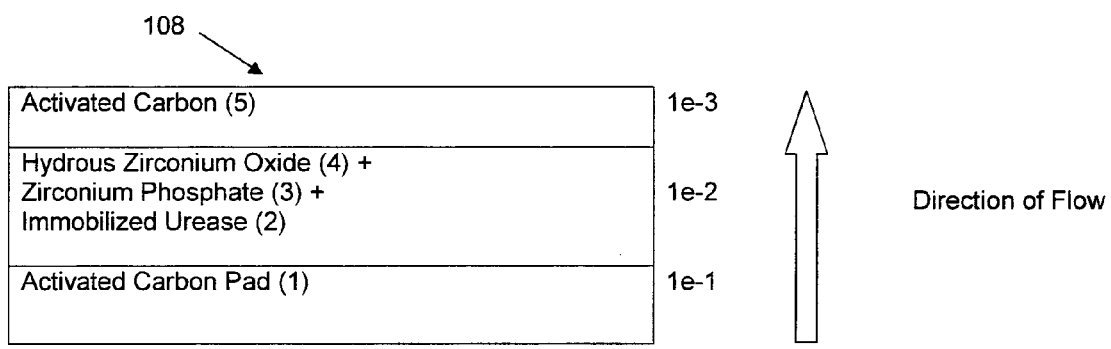

Referring now to FIG. 1e, there is shown another embodiment of the sorbent (108) used. The activated carbon pad (1), immobilized urease (2), zirconium phosphate particles (3), hydrous zirconium oxide particles (4), activated carbon particles (5) and the respective substrates used for the following layers are the same as those described above for FIG. 1a.

An activated carbon pad (1) in the first layer (1e-1) is same to that of FIG. 1a elaborated above.

In the second layer (1e-2) of the sorbent (108) is arranged in series, adjacent to the first layer (1e-1). The second layer (1e-2) comprises a mixture of immobilized urease particles (2), zirconium phosphate particles (3) and hydrous zirconium oxide particles (4). The total weight range of urease particles (2) is from 0.5 to 30 grams. The total weight of the zirconium phosphate particles (3) is from about 100 grams to 1000 grams. The total weight range of the hydrous zirconium oxide particles (4) is from about 10 grams to 100 grams. The third layer (1e-3) of the sorbent (108) is arranged in series, adjacent to the second layer (1e-2). The third layer (1e-3) comprises activated carbon particles (5) which is same to that (1b-4) of FIG. 1b. The total weight range of the activated carbon particles (5) is from about 20 grams to 200 grams.

When in use, the sorbent (108) is arranged in the dialysis device such that direction of the dialysate flow is from the first layer (1e-1) to the third layer (1e-3) as shown by the arrow. As the dialysate passes into the first layer (1e-1), this layer removes enzyme inhibiting substances and toxins, same as in the description above (FIG. 1a). When the dialysate enters into the second layer (1e-2), the mixture of the urease particles (2), zirconium phosphate particles (3) and hydrous zirconium oxide particles (4) removes urea, cations such as ammonium ions, calcium, magnesium and potassium and anions such as phosphate and fluoride. Advantageously, mixing of immobilized urease and both types of ion exchangers in one combined layer significantly improves the performance by facilitating immediate toxin absorption and producing more consistent pH conditions in the dialysate throughout the sorbent's use. Meanwhile this mixture also reduces the size of the sorbent (108) without compromising the toxin removal capability. When the dialysate passes into the final layer (1e-3) of the sorbent (108), the activated carbon particles (5) absorb creatinine, uric acid and other uremic toxins present in the dialysate.

Figure 1F:
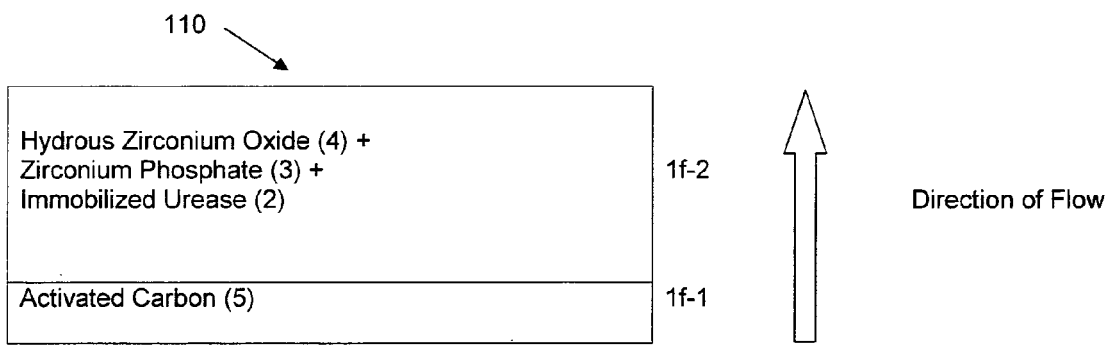

Referring now to FIG. 1f, there is shown another embodiment of the sorbent (110) used. The immobilized urease (2), zirconium phosphate particles (3), hydrous zirconium oxide particles (4), activated carbon particles (5) and the respective substrates used for the following layers are the same as those described above for FIG. 1a.

A first layer of activated carbon particles (5) is the same to that described above (FIG. 1c).

The second layer (1f-2) of the sorbent (110) is arranged in series, adjacent to the first layer (1f-1). The second layer (1f-2) comprises a mixture of immobilized urease particles (2), zirconium phosphate particles (3) and hydrous zirconium oxide particles (4). The total weight range of urease particles (2) is from 0.5 to 30 grams. The total weight of the zirconium phosphate particles (3) is from about 100 grams to 1000 grams. The total weight range of the hydrous zirconium oxide particles (4) is from about 10 grams to 100 grams.

When in use, the sorbent (110) is arranged in the dialysis device such that direction of the dialysate flow is from the first layer (1f-1) to the second layer (1f-2) as shown by the arrow. As the dialysate passes into the first layer (1f-1), this layer removes enzyme inhibiting substances as well as creatinine, uric acid and other uremic toxins present in the dialysate, as in the description above (FIG. 1c). When the dialysate enters into the second layer (1f-2), the mixture of the urease particles (2) and zirconium phosphate particles (3) and hydrous zirconium oxide particles (4) removes urea, cations such as ammonium ions, calcium, magnesium and potassium, and anions such as phosphate and fluoride in the same way as described above (FIG. 1e). The advantage herein is same as the description above (FIG. 1e).

Figure 1G:
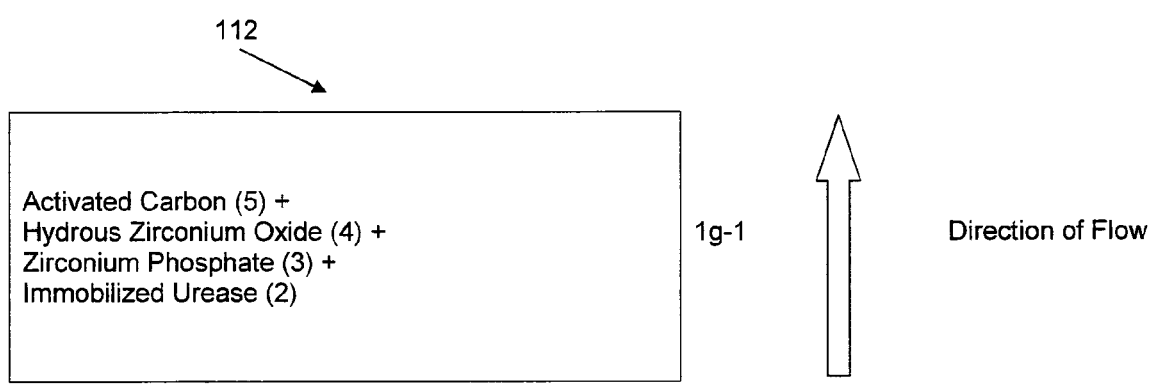

Referring now to FIG. 1g, there is shown another embodiment of the sorbent (112) used. The activated carbon particles (5), immobilized urease particles (2), zirconium phosphate particles (3), hydrous zirconium oxide particles (4) and the respective substrates used for the following layers are the same as those described above for FIG. 1a.

There is one homogenous filling (1g-1) for the sorbent (112). The filling layer (1g-1) is a homogenous mixture of immobilized urease particles (2), zirconium phosphate particles (3), hydrous zirconium oxide particles (4) and activated carbon particles (5). The total weight range of urease particles (2) is from 0.5 grams to 30 grams; the total weight of the zirconium phosphate particles (3) is from about 100 grams to 1000 grams; the total weight range of the hydrous zirconium oxide particles (4) is from about 10 grams to 100 grams; the total weight range of activated carbon particles is from 20 grams to 200 grams.

When in use, the sorbent (112) is arranged in the dialysis device such that direction of the dialysate flow is from the bottom dimension to the top dimension (1g-1) as shown by the arrow. As the dialysate passes through the sorbent (112), the mixture of the immobilized urease particles (2), zirconium phosphate particles (3), hydrous zirconium oxide particles (4) and activated carbon particles (5) removes urea, cations such as ammonium ions, calcium, magnesium and potassium, anions such as phosphate and fluoride, and enzyme inhibiting substances and small to medium size organic metabolites, such as creatinine, uric acid and other uremic toxins. This arrangement gives the benefits of an improved performance of both particles as a buffer, thus producing more consistent pH conditions in the dialysate throughout the sorbent's use. More advantageously, mixing of immobilized urease, both types of ion exchangers and activated carbon in one combined layer gives the benefits of a much more compact size of the sorbent (112) and sufficient toxin removal capability. It also reduces the pressure drop caused by the sorbent to a minimum, and facilitates the production process significantly. It eliminates the risk of having uneven sorbent layers, which would be a cause for premature exhaustion of the sorbent layers.

Figure 2A:
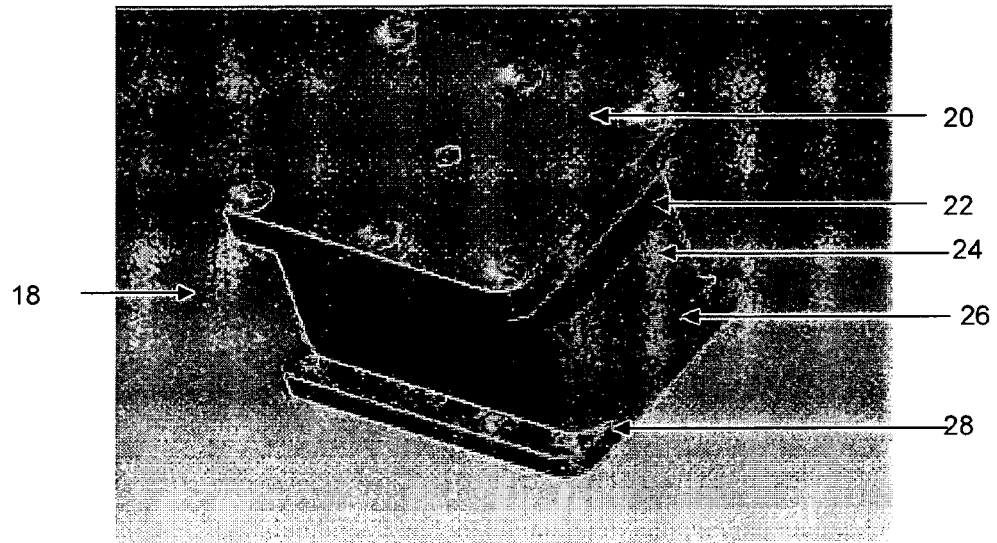
Figure 2B:
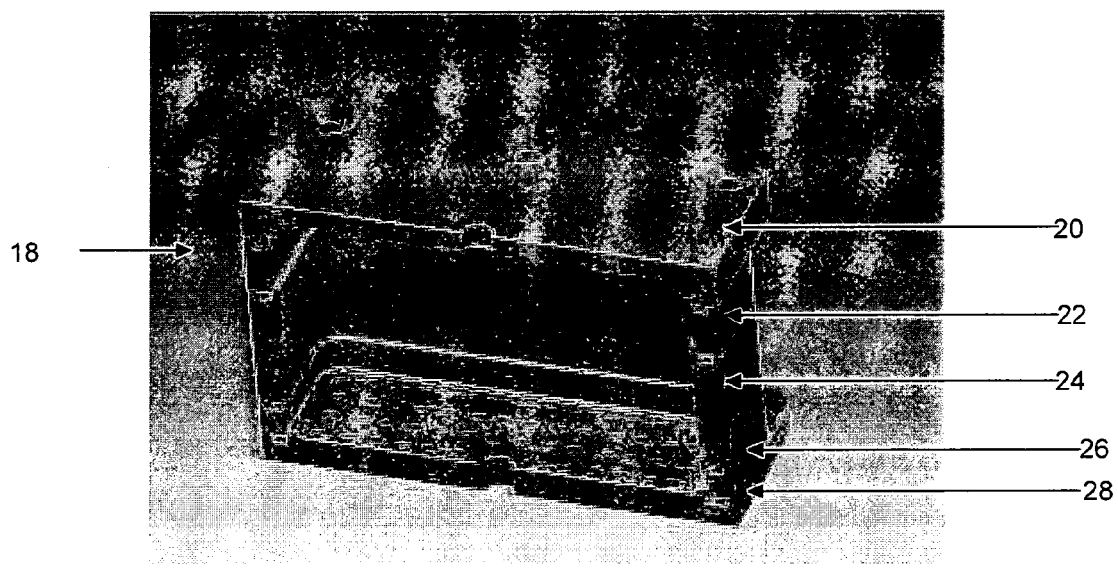

Referring to FIG. 2a and FIG. 2b, there is shown a cartridge (18), for housing the sorbent (102) as described above. The cartridge (18) is made of polycarbonate. The top (20) of the cartridge (18) and the bottom of the cartridge (28) have flanges for slotting into the dialysis device. The interior of the cartridge (18) is divided into three compartments. The first compartment (26) houses the mixture of immobilized urease (16) and zirconium phosphate particles (14). The first compartment has a height of 27 mm, a length of 113 mm and a breadth of 57 mm. The second compartment (24) houses the zirconium phosphate particles (14). The second compartment (24) has a height of 27 mm, a length of 113 mm and a breadth of 57 mm. The third compartment (22) the mixture of activated carbon particles (10) and hydrous zirconium oxide particles (12). The third compartment (22) has a height of 13 mm, a length of 113 mm and a breadth of 57 mm.

Figure 2C:
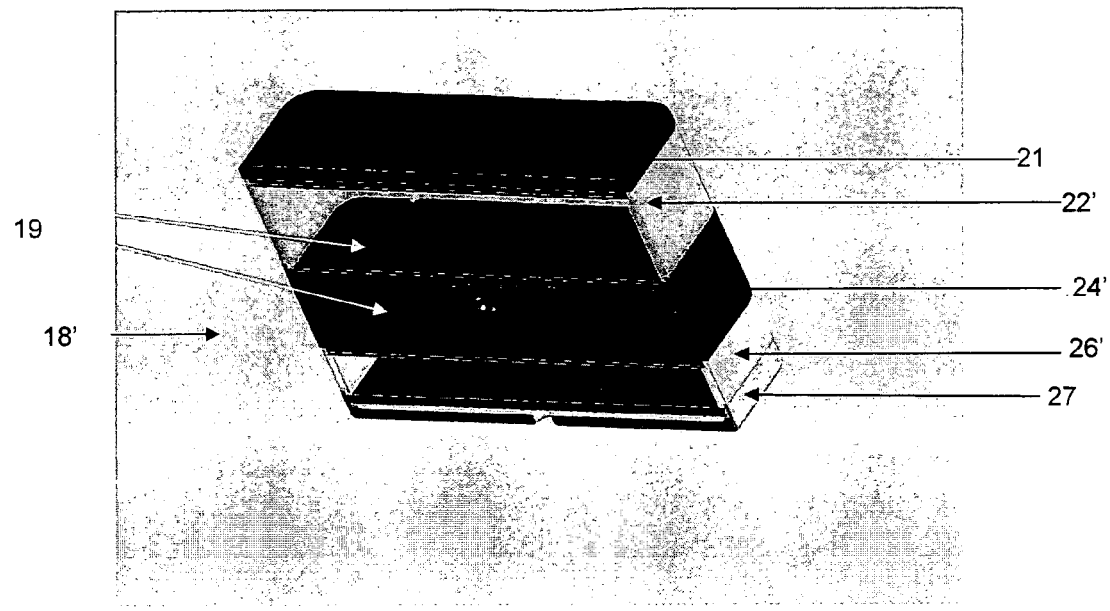
FIG. 2c is a cross sectional view of a CAD of another embodiment of the sorbent cartridge having partitions to demarcate the different layers of the sorbent.

Referring now to FIG. 2c, there is shown a cross sectional view of a cartridge 18' having a number of technical features that are the same as the cartridge 18 described above which are indicated by the same reference numeral but with a prime symbol ('). The bottom (27) and top (21) of cartridge 18' do not contain flanges and have reduces the overall external dimensions of the cartridge (18'). The cartridge (18') can be inserted in the dialysis device and secured by fastening means such as nuts and bolts. The cartridge (18') also contains separators (19) for a better demarcation of the different layers of the sorbent.

Figure 3:
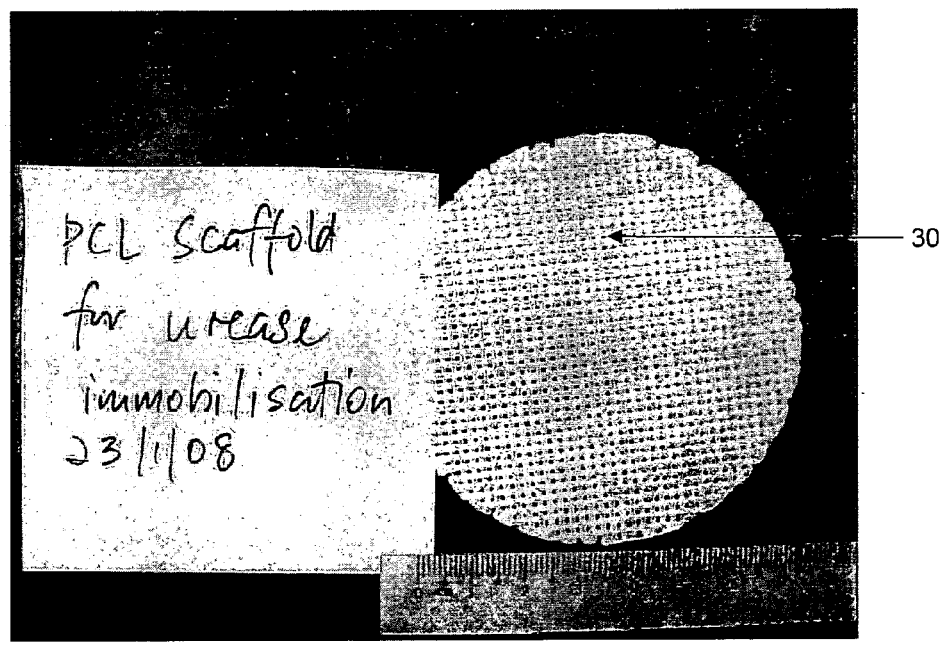
FIG. 3 shows a polycarpolactone (PCL) scaffold for use as a biocompatible substrate for the immobilization of urease as disclosed herein.

Referring now to FIG. 3, there is shown a PCL scaffold or substrate (30) used for urease immobilization as described above. The PCL scaffold (30) has a diameter of about 7 cm.

Figure 4:
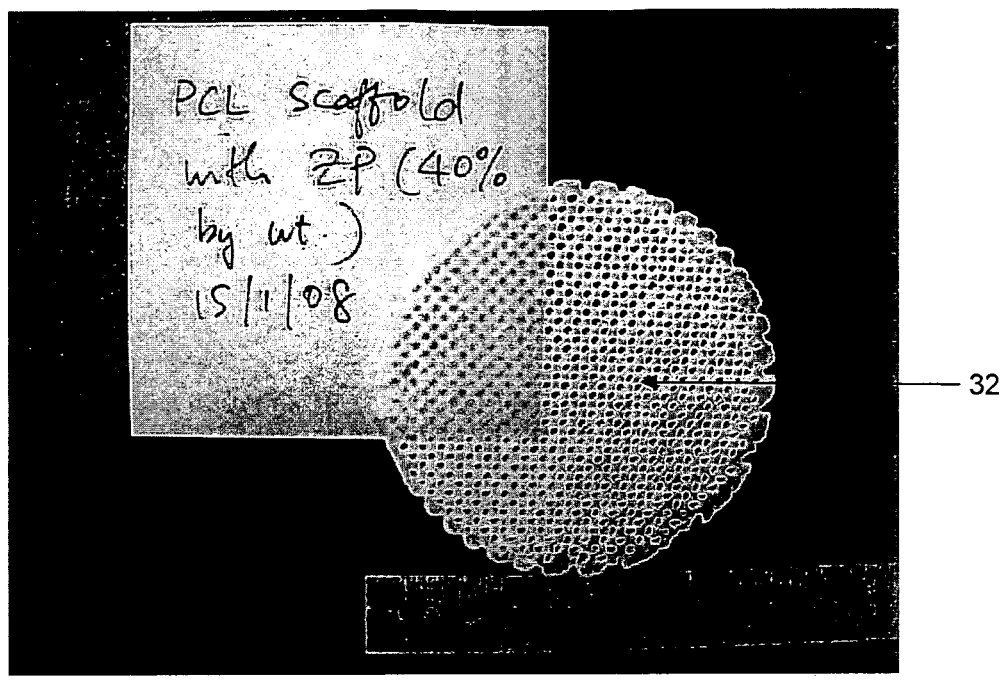
FIG. 4 shows a polycarpolactone (PCL) scaffold for use as a biocompatible substrate for the immobilization of zirconium phosphate as disclosed herein.

Referring to FIG. 4, there is shown a PCL scaffold (32) containing 40% zirconium phosphate. The PCL scaffold (32) has a diameter of about 7 cm.

Examples

Evidence of Improved Urease Activity and Stability by Mixing Immobilised Urease (IU) and Zirconium Phosphate (ZP)

TABLE 1

| Pure IU | | | |
|---|---|---|---|
| | 3 h | 5 h | 10 h |
| pH | 8.6 | 8.6 | 8.6 |
| Urea removal | 94% | 98% | 86% |
| Pressure drop | 20 mmHg | 30 mmHg | 120 mmHg |

TABLE 2

| One layer pure IU, one layer pure ZP | | | |
|---|---|---|---|
| | 3 h | 5 h | 10 h |
| pH | 7.6 | 8.22 | over-pressure |
| Urea removal | 99% | 99% | over-pressure |
| Pressure drop | 70 mmHg | 720 mmHg | over-pressure |

TABLE 3

| IU and ZP, one mixed layer | | | |
|---|---|---|---|
| | 3 h | 5 h | 10 h |
| pH | 7.6 | 8.5 | 8.5 |
| Urea removal | 100% | 99% | 98% |
| Pressure drop | 70 mmHg | 70 mmHg | 70 mmHg |

From the above data, it can be seen that when IU and ZP are mixed in one layer, a high level of urea removal can be achieved over a long period of time (10 h), while maintaining a relatively stable pressure drop across the sorbent as shown in Table 3. On the other hand, when IU is used alone, the urea removal efficiency decreases over time and the pressure drop across the sorbent increases significantly over time as shown in Table 1. In the case when IU and ZP are used but in separate layers, although the urea removal efficiency is maintained at a high level, drastic pressure drops occurs over time across the sorbent as shown in Table 2, leading to overpressure and damage to the sorbent and/or the dialysis device.

Study of Absorbance Capacity of Zirconium Phosphate in Dependence of Particle Size

TABLE 4

| 10 g ZP (batch PP835A-Nov08), 0.3 L/h, 12 mmol/L NH4+ | | |
|---|---|---|
| Particle Size | Pressure Drop | Absorbance Capacity (mmol NH4+ per g ZP) |
| <50 μm | 460-500 mmHg | 0.84 mmol/g |
| 50-100 μm | 80-120 mmHg | 0.90 mmol/g |

TABLE 5

| 10 g ZP (batch PP911C-Jan09), 0.3 L/h, 12 mmol/L NH4+ | | |
|---|---|---|
| Particle Size | Pressure Drop | Absorbance Capacity (mmol NH4+ per g ZP) |
| <50 μm | 340-360 mmHg | 0.90 mmol/g |
| 50-100 μm | 140-160 mmHg | 0.91 mmol/g |
| 100-150 μm | 30-50 mmHg | 0.83 mmol/g |
| 150-200 μm | 20-30 mmHg | 0.79 mmol/g |

The pressure drop caused by zirconium phosphate particles is shown to be strongly dependent of the particle size of the zirconium phosphate under consideration. Thus, while layers of particles of less than 50 microns size produce unacceptably high pressure drops, particle sizes of 50 to 100 microns already produce significantly lower pressure drops in a favourable range for application in the sorbent cartridge. Increasing the particle size to 100 to 150 microns, and 150 to 200 microns further reduces the pressure drop caused by the particles under consideration. Moreover, it can be seen from above data that the absorbance capacity of the zirconium phosphates under consideration is highest for particles of 50 to 100 microns size. The optimum between ammonia absorption capacity and pressure drop is therefore at zirconium phosphate particle sizes of 50 to 100 microns.

Study of Absorbance Capacity of Hydrous Zirconium Oxide in Dependence of Particle Size

TABLE 6

| 2 g HZO (batch ZrOH 304-AC - Mar09), 0.3 L/h, 1.0 mmol/L P | | |
|---|---|---|
| Particle Size | Pressure Drop | Absorbance Capacity (mmol P per g HZO) |
| <50 μm | 30-40 mmHg | 0.68 mmol/g |
| 50-100 μm | 20-30 mmHg | 0.63 mmol/g |

The pressure drop caused by hydrous zirconium oxide particles is shown to be significantly lower than that caused by the zirconium phosphate particles, even at particle sizes of smaller than 50 microns. This is partly due to the smaller quantity of hydrous zirconium oxide required for the cartridge functionality. Thus, a layer of hydrous zirconium oxide particles of less than 50 microns (>95% within 10 to 50 microns) size produces an acceptable pressure drop for use in the cartridge, while particles of this size also show improved phosphate absorbance capacity over particles of greater than 50 microns size. The preferred particle size for application in the sorbent cartridge is therefore 10 to 50 microns.

Study of Absorbance Capacity of Activated Carbon in Dependence of Particle Size

The capacity of activated carbon to absorb creatinine is shown to be dependent on the flow rate of dialysate and on the particle size of the carbon under consideration. Crucially, there is a tendency for higher capacity, and increasing pressure drop with smaller particle size. The optimum between acceptable pressure drop and maximum absorbance is at a particle size range of 50-100 μm as shown in the experimental results tabulated below.

Series 1
Activated carbon from Calgon, first batch
Conditions:
Synthetic hemodialysate containing 135 μmol/l creatinine, 37° C.

TABLE 7

| Particle Size | Amount Carbon | Flow Rate | Absorbed Creatinine | Absorbance Capacity (μmol Creatinine per g Carbon) |
|---|---|---|---|---|
| 0-50 μm | 2 g | 0.6 l/h | Nil (over-pressure) | |
| 50-100 μm | 3 g | 0.6 l/h | 440 μmol | 145 μmol/g |
| 100-150 μm | 4 g | 0.6 l/h | 450 μmol | 110 μmol/g |
| 150-200 μm | 5 g | 0.6 l/h | 460 μmol | 100 μmol/g |
| 200-300 μm | 6 g | 0.6 l/h | 440 μmol | 70 μmol/g |
| 300-1000 μm | 10 g | 0.6 l/h | 450 μmol | 60 μmol/g |
| 1000-2000 μm | 10 g | 0.6 l/h | 300 μmol | 30 μmol/g |

Series 2
Activated carbon from Calgon, second batch
Conditions:
Synthetic hemodialysate containing 135 μmol/l creatinine, 37° C.

TABLE 8

| Particle Size | Amount Carbon | Flow Rate | Absorbed Creatinine | Absorbance Capacity (μmol Creatinine per g Carbon) |
|---|---|---|---|---|
| 0-100 μm | 2 g | 0.6 l/h | 80 μmol | 40 μmol/g |
| 100-200 μm | 4 g | 0.6 l/h | 220 μmol | 55 μmol/g |
| 200-500 μm | 4 g | 0.6 l/h | 140 μmol | 35 μmol/g |

Series 3
Activated carbon from Sorb
Conditions:
Synthetic hemodialysate containing 110 μmol/l creatinine, 37° C.

TABLE 9

| Particle Size | Amount Carbon | Flow Rate | Absorbed Creatinine | Absorbance Capacity (μmol Creatinine per g Carbon) |
|---|---|---|---|---|
| 0-100 μm | 2 g | 0.6 l/h | 242 μmol | 121 μmol/g |
| 100-200 μm | 4 g | 0.6 l/h | 320 μmol | 80 μmol/g |
| 200-500 μm | 4 g | 0.6 l/h | 275 μmol | 70 μmol/g |
| 1000-2000 μm | 37 g | 6.0 l/h | 275 μmol | 7 μmol/g |

Layout and Design of Sorbent Cartridge

The Sorbent cartridge disclosed herein is designed to remove urea and other waste materials that are present in the spent dialysate and enable the regeneration of the dialysate for its repeated use in dialysis. This will reduce the amount of dialysate used in conventional modalities of about 120 liters in a 4-hour haemodialysis session or 70 to 100 liters in a week typical peritoneal dialysis. In hemodialysis, the cartridge can be used to regenerate the dialysate that will pass through the hemodialyzer. The dialysate can be regenerated into a reservoir of the dialysate for reconstitution and continued use in dialysis. In peritoneal dialysis, the cartridge can be used to regenerate the dialysate withdrawn from the patient's peritoneal cavity. The regenerated dialysate may then be made available to reconstitution systems allowing its re-introduction into the patient's cavity.

The sorbent cartridge is designed, in terms of size and weight, to be wearable with the carrier disclosed herein when inserted in the dialysis device (collectively known as the wearable peritoneal dialysis machine or WPDM). This enables patients to be more mobile in carrying out their daily activities and to be more economically productive. The dialysis device comprising the disclosed sorbent can remove uremic toxins 24/7, and is effective in removal of the uremic toxins in comparison to any other current modalities available in the market.

From experiment carried out, it is observed that the sorbent disclosed herein is able to absorb 190 mmol of urea (or 5.3 grams of urea-N). The sorbent cartridge is also a sterile, single use unit, used individually or in combination with the prescribed amount of glucose to be incorporated, through the enrichment module in the WPDM. In summary, the preferred sorbent layouts, quantity of the components in each layer and function are represented in the following tables:

TABLE 10

General principle

| | | Function | |
|---|---|---|---|
| | Quantity, g | Removes from the Dialysate | Release into the Dialysate |
| Regenerated Dialysate ⇧ Flow Direction | | | |
| Hydrous Zircinium Oxide (HZO) and Activated Carbon (AC) | HZO: 10 to 100 AC: 20 to 200 | Creatinine, uric acid, phosphate and organic molecules | Acetate |
| Zirconium Phosphate (ZP) | ZP: 100 to 1000 | Ammonia, calcium, magnesium and potassium | Sodium- and hydrogen-ions |
| Immobilized Urease (IU) and Zirconium Phosphate (ZP) | IU: 0.5 to 30 ZP: 100 to 1000 | Urea, ammonium, calcium, magnesium and potassium | Ammonium carbonate, sodium- and hydrogen-ions |
| Spent Dialysate ⇧ Flow Direction | | | |

In Vitro Test

1. Purpose

The purpose of the in-vitro test is to verify the sorbent cartridge's functionality under conditions simulating its application in the regeneration of patient hemodialysisate. To this end, the patient spent dialysate is replaced by synthetic spent hemodialysate, containing the uremic toxins urea, creatinine and phosphate in the expected concentrations for continuous hemodialysis.

TABLE 11

2. Cartridge composition

| | Quantity, g |
|---|---|
| Regenerated Dialysate ⇧ Flow Direction | |
| Activated Carbon (AC) | 55 g |
| Hydrous Zirconium Oxide (HZO) | 60 g |
| Zirconium Phosphate (ZP) | 335 g |
| Immobilized Urease (IU) and | IU: 6 g |

TABLE 11-continued

2. Cartridge composition

| | Quantity, g |
|---|---|
| Zirconium Phosphate (ZP) | ZP: 120 g |
| Activated Carbon (AC) | Pad, 3 mm thickness |
| Spent Dialysate ↑ | |
| Flow Direction | |

3. In Vitro Test Conditions

The test was conducted at a dialysate temperature of 37° C. and a continuous flow rate of 6.0 L/h. Exhaustion is defined as the point where at least one of the chemical components of the regenerated dialysate is out of the acceptable range (see 3.2 below).

The following tables show the composition of a typical spent hemo-dialysate, the medically accepted ranges for the components of regenerated dialysate and the quantities of the absorbed toxins when spent dialysate is passed through one embodiment of the sorbent disclosed herein (Table 11).

TABLE 12

3.1. Composition of Synthetic Spent Hemo--Dialysate

| | SI units | Alternative Units |
|---|---|---|
| Component | | |
| Na | 140 mmol/L | 140 mEq/L |
| Ca | 1.50 mmol/L | 3.00 mEq/L |
| Mg | 0.50 mmol/L | 1.00 mEq/L |
| K | 2.00 mmol/L | 2.00 mEq/L |
| Cl | 111 mmol/L | 111 mEq/L |
| HCO3 | 31 mmol/L | 31 mEq/L |
| Glucose | 11.1 mmol/L | 200 mg/dL (anhydrous) |
| | | 220 mg/dL (dextrose) |
| Toxins | | |
| Urea | 6.00 mmol/L | 36.0 mg/dL urea |
| | | 16.8 mg/dL urea-N |
| Creatinine | 203 µmol/L | 1.53 mg/dL creatinine |
| Phosphate | 720 µmol/L | 1.49 mg/dL P |

TABLE 13

3.2. Acceptable Range for Regenerated Dialysate (post sorbent cartridge)

| | SI units | Alternative Units |
|---|---|---|
| Component | | |
| Na | 120-150 mmol/L | 120-150 mEq/L |
| Ca | 0 mmol/L | 0 mEq/L |
| Mg | 0 mmol/L | 0 mEq/L |
| K | 0 mmol/L | 0 mEq/L |
| Cl | 111 mmol/L | 90-115 mEq/L |
| HCO3 | 5-37 mmol/L | 5-37 mEq/L |
| Glucose | 0-13 mmol/L | 0-234 mg/dL (anhydrous) |
| | | 0-258 mg/dL (dextrose) |
| Toxins | | |
| Urea | 0-0.60 mmol/L | 0-3.60 mg/dL urea |
| | | 0-1.68 mg/dL urea-N |
| Creatinine | 0-20 µmol/L | 0-0.23 mg/dL creatinine |
| Phosphate | 0-70 µmol/L | 0-0.22 mg/dL P |
| Ammonia (from urea) | 0-1.4 mmol/L | 0-2 mg/dL N |

4. Test Results

Exhaustion: The ammonia concentration in the cartridge outflow was greater than 1.4 mmol/L (2.0 mg/dL) after a total of 32 L of synthetic spent dialysate has passed through the sorbent cartridge. All other analytes were still within the acceptable limits.

TABLE 14

4.1. Total Amounts of Absorbed Toxins at the Time of Exhaustion

| Toxins | SI units | Alternative Units |
|---|---|---|
| Urea | 190 mmol | 11.4 g urea |
| | | 5.3 g urea-N |
| Creatinine | 6.6 mmol | 750 mg creatinine |
| Phosphate | 23 mmol | 710 mg P |

TABLE 15

4.2. pH, Sodium and Bicarbonate Balance at time of exhaustion, and Pressure Drop

| Component | SI units | Alternative Units |
|---|---|---|
| pH | 6.3-7.2 | |
| Na | 250 mmol total release | 250 mEq total release |
| HCO3 | 70 mmol total release | 70 mEq total release |
| Pressure Drop | 140-170 mmHg | |

5. Conclusion

The performance of the sorbent cartridge met or exceeded all requirements defined in 3.2 and 3.3 above for use in the regeneration of spent hemodialysate. It had a total capacity of 5.3 g urea-N, 750 mg creatinine and 710 mg phosphate-P.

APPLICATIONS

The disclosed sorbent for a dialysis device may be used for peritoneal dialysis or hemodialysis. Advantageously, the disclosed sorbent when used in a dialysis device is capable of removing protein-bound toxins which is usually not possible with several known dialysis devices.

The disclosed sorbent is a compact and portable sorbent that, when used in the WPDM (wearable peritoneal dialysis machine), is capable of absorbing all of the urea, phosphate, creatinine and other uremic toxins produced by the patient and present in the dialysate, providing optimal clearance for uremic toxins. Advantageously, the sorbent is configured in a manner that achieves compactness without compromising on its capacity to remove metabolic waste from the dialysate quickly and effectively. In one preferred embodiment, that is, when the immobilised urease and zirconium phosphate particles coexist in one layer of the sorbent, an optimal working environment is created for the immobilized urease as the zirconium phosphate particles act as buffer to counteract any pH changes. Advantageously, this increases urease activity and prolongs the life of the immobilized urease. More advantageously, as this specific configuration involves the combination of one or more materials in the layers of the sorbent, the overall size of the sorbent is reduced significantly. As a result, the portability of the dialysis device is improved, thereby providing greater patient mobility. At the same time, the zirconium phosphate particles also act as cation exchangers and remove unwanted cations from the dialysate.

In one embodiment, the zirconium phosphate particles provided have an average particle size of 25 microns to 100 microns. Advantageously, this specific particle size range has been found by the inventors to increase the efficacy of the unwanted cation removal capabilities of the zirconium phosphate particles.

While reasonable efforts have been employed to describe equivalent embodiments of the present invention, it will be apparent to the person skilled in the art after reading the foregoing disclosure, that various other modifications and adaptations of the invention may be made therein without departing from the spirit and scope of the invention and it is intended that all such modifications and adaptations come within the scope of the appended claims.

The invention claimed is:

1. A fixed bed sorbent for removing metabolic waste products from a dialysis liquid, the sorbent comprising a primary layer of urease particles covalently immobilized on a biocompatible material intermixed with cation exchange particles and anion exchange particles, wherein the cation exchange particles are zirconium phosphate particles and the anion exchange particles are zirconium oxide particles, wherein a pressure drop of the dialysis liquid across the primary layer is dependent on the size of said cation exchange particles; and wherein said urease uremic toxin-treating enzyme particles, said anion exchange particles and said cation exchange particles are, when in use, in direct contact with the dialysis liquid.

2. The fixed bed sorbent as claimed in claim 1 further comprising a secondary layer of organic compounds absorber particles.

3. The fixed bed sorbent as claimed in claim 2, wherein the direction of the dialysis liquid flow is from said primary layer to said secondary layer.

4. The fixed bed sorbent as claimed in claim 2, wherein said organic compounds absorber particles are activated carbon particles.

5. The fixed bed sorbent as claimed in claim 1, wherein said urease particles are immobilized on at least one of cellulose, nylon, polycaprolactone and chitosan.

6. The fixed bed sorbent as claimed in claim 1, wherein said zirconium oxide is hydrous zirconium oxide.

7. The fixed bed sorbent as claimed in claim 1, wherein said urease particles have an average particle size in the range of from 10 microns to 1000 microns.

8. The fixed bed sorbent as claimed in claim 1, wherein said zirconium phosphate particles have an average particle size in the range of from 10 microns to 1000 microns.

9. The fixed bed sorbent as claimed in claim 1, wherein said zirconium oxide particles have particle size in the range of from 10 microns to 1000 microns.

10. The fixed bed sorbent as claimed in claim 4, wherein said activated carbon particles have an average particle size in the range of from 10 microns to 1000 microns.

11. A fixed bed sorbent for removing metabolic waste products from a dialysis liquid, the sorbent comprising a layer of urease particles covalently immobilized on a biocompatible material intermixed with cation exchange particles having an average particle size in the range of 50 microns to 200 microns and anion exchange particles;

wherein the cation exchange particles are zirconium phosphate particles and the anion exchange particles are zirconium oxide particles, and wherein said urease particles, said anion exchange particles and said cation exchange particles are, when in use, in direct contact with the dialysis liquid.

* * * * *

UNITED STATES PATENT AND TRADEMARK OFFICE
CERTIFICATE OF CORRECTION

| | | |
|---|---|---|
| PATENT NO. | : 9,242,036 B2 | Page 1 of 1 |
| APPLICATION NO. | : 13/000811 | |
| DATED | : January 26, 2016 | |
| INVENTOR(S) | : Christian Gert Bluchel et al. | |

It is certified that error appears in the above-identified patent and that said Letters Patent is hereby corrected as shown below:

Claims:

In claim 1, column 23, line 27 delete "uremic toxin-treating enzyme".

Signed and Sealed this
Seventeenth Day of May, 2016

Michelle K. Lee
*Director of the United States Patent and Trademark Office*